United States Patent [19]

Patel et al.

[11] Patent Number: 4,769,459

[45] Date of Patent: Sep. 6, 1988

[54] OXIDATIVE IMAGING

[75] Inventors: Ranjan C. Patel, Thorley; Ian J. Ferguson, Ickleton; Herbert J. Pennicott, Harlow, all of United Kingdom

[73] Assignee: Minnesota Mining and Manufacturing Company, St. Paul, Minn.

[21] Appl. No.: 926,338

[22] Filed: Nov. 3, 1986

Related U.S. Application Data

[62] Division of Ser. No. 814,635, Dec. 30, 1985, Pat. No. 4,701,402.

[51] Int. Cl.$^4$ .............................................. C07D 239/02

[52] U.S. Cl. .................................... 544/301; 544/296; 558/443; 548/146; 548/358; 549/33

[58] Field of Search ................. 544/290, 301; 558/443

[56] References Cited

U.S. PATENT DOCUMENTS

| | | | |
|---|---|---|---|
| 2,533,472 | 12/1950 | Keyes et al. | 230/522 |
| 4,384,034 | 5/1983 | Ferguson et al. | 430/900 |
| 4,515,888 | 5/1985 | Beretta et al. | 430/584 |
| 4,548,896 | 10/1985 | Sabongi et al. | 430/332 |

FOREIGN PATENT DOCUMENTS 779065 7/1957 United Kingdom .

OTHER PUBLICATIONS

Merck Index, 10th edition, 5933–Methylene Blue.

*Primary Examiner*—Donald G. Daus
*Assistant Examiner*—Cecilia Shen
*Attorney, Agent, or Firm*—Donald M. Sell; Mark A. Litman

[57] ABSTRACT

A radiation-sensitive element capable of recording an image upon image-wise exposure to radiation of selected wavelength, the element comprising, as the image-forming components, an effective amount of a bleachable dye in reactive association with an iodonium ion. Suitable dyes include polymethine dyes having an oxidation potential between 0 and +1 volt.

7 Claims, No Drawings

OXIDATIVE IMAGING

This is a division of application Ser. No. 814,635, filed Dec. 30, 1985, now U.S. Pat. No. 4,701,402.

FIELD OF THE INVENTION

This invention relates to radiation-sensitive elements which are capable of recording a positive image upon image-wise exposure to radiation, e.g. visible light, and to their preparation and use. In particular, the invention relates to radiation-sensitive elements having a bleachable dye and an iodonium salt in reactive association.

BACKGROUND OF THE INVENTION

Positive working imaging systems in which an originally coloured species is decolourised in an image-wise manner are known. These systems have the advantage of giving a positive copy of an original. One of the earliest forms of positive working imaging systems was developed utilising the properties of photographic silver, e.g. as disclosed in British Patent Specification No. 17773 (1889), Austrian Patent Specification No. OE42478 and B. Gaspar, Zeitschrift Wiss. Phot. 34, 119 (1935). Since then many forms of colour silver halide photography have been developed.

Silverless dye bleaching processes are also known, but in spite of the apparent simplicity of these systems, they have encountered a number of problems. The inadequate photosensitivity of such systems consisting of colour layers, the lack of purity and stability of the white in the final print and difficulty of finding dyes which form a neutral grey and bleaching at equal rates, are some of the problems. Early systems are disclosed in Smith, Photogr. J., April 1910, page 141. More recently, cyanines with borate anions are disclosed as a dye bleach system in British Patent Specification Nos. 1 370 058, 1 370 059 and 1 370 060. A dye bleach process involving tetra(alkyl)borate is disclosed in U.S. Pat. No. 4,307,182 and fixing methods are disclosed in European Patent Specification No. 0040978. U.S. Pat. No. 3,595,655 discloses a silverless dye bleach system consisting essentially of a polymethine dye and an activator which is a carbonyl, azo, diazo, organic-sulphur containing or peroxide compound.

It is an object of the present invention to provide new radiation-sensitive elements capable of recording a positive image.

SUMMARY OF THE INVENTION

Therefore according to the invention there is provided a radiation-sensitive element capable of recording an image upon image-wise exposure to radiation of selected wavelength, the element comprising, as the image-forming components, an effective amount of a bleachable dye in reactive association with an iodonium ion.

The elements of the invention are capable of recording a positive image simply upon exposure to radiation of selected wavelength; the radiation absorbed by the dye which is in reactive association with an iodonium ion causes the dye to bleach. The dyes are believed to sensitise spectrally the reduction of the iodonium ion through the radiation absorbed by the dyes associated with the iodonium ion. Thereafter the element may be stabilised to fix the image by destruction of the iodonium ion or by separation of the dye relative to the iodonium ion.

The dyes used in the invention may be of any colour and any chemical class which is capable of bleaching upon exposure to radiation of selected wavelength in the presence of an iodonium ion.

By a suitable selection of dye an element of the invention may be prepared which is sensitive to radiation of a selected wavelength band within the general range 300 to 1000 nm, the particular wavelength and the width of the band depending upon the absorption characteristics of the dye. In general, where a dye has more than one absorption peak it is the wavelength corresponding to the longest wavelength peak at which one would choose to irradiate the element.

Elements intended for the production of images from radiation in the visible region (400 to 700 nm) will contain dyes which will bleach from a coloured to a substantially colourless or very pale state. In practice, such bleachable dyes will undergo a change such that the transmission optical density at the $\lambda_{max}$ will drop from 1.0 or more to less than 0.09, preferably less than 0.05. The dyes will generally be coated on the support to provide an optical density of about 3.0 or more.

In the case of elements sensitive to ultraviolet radiation (300 to 400 nm) the dyes will not normally be coloured to the eye and there may be no visible change upon exposure to ultraviolet radiation and bleaching. The image-wise exposed elements may be used as masks for further ultraviolet exposure after fixing.

Infrared sensitive elements of the invention contain dyes have an absorption peak in the wavelength range 700 to 1100 nm. These dyes may also have absorption peaks in the visible region before and/or after bleaching. Thus, as well as providing a means for obtaining masks for subsequent infrared exposure in a similar manner to the ultraviolet masks, infrared sensitive elements of the invention may record a visible image upon image-wise exposure to infrared radiation.

Certain of the elements of the invention, e.g. those containing oxonol or cyanine dyes, will bleach upon heating and may be used as heat bleachable antihalation layers or to record thermal images. The heat bleaching effect of dye/iodonium ion combination may also be utilised as a method of fixing a visual image obtained with a different dye by reacting the excess iodonium ion upon heating.

The dyes used in the invention may be anionic, cationic or neutral. Preferred dyes are anionic since they give very good photosensitisation which is believed to be due to an intimate reactive association between the negatively charged dye and the positively charged iodonium ion. Also anionic dyes may readily be mordanted to cationic polymer binders and it is relatively simple to remove surplus iodonium ions in an aqueous bath in a fixing step if the mordanting polymer is cationic. However, neutral dyes also give good results and are preferred over cationic dyes for overall photosensitivity. Cationic dyes are least preferred since it is more difficult to achieve intimate reactive association between the positively charged dye and iodonium ion, and selective removal of iodonium ion after imaging is more difficult.

The bleachable dyes may be generically referred to as polymethine dyes which term characterises dyes having at least one electron donor and one electron acceptor group linked by methine groups or aza analogues. The dyes have an oxidation potential between 0 and +1 volt, preferably between +0.2 and +0.6 volt. The bleachable dyes may be selected from a wide range of known classes of dyes including allopolar cyanine dye bases, complex cyanine, hemicyanine, merocyanine, azine, oxonol, streptocyanine and styryl.

Three species of dye are of particular significance for use in the invention. These species are dyes which include within their structure one of the following systems:

(1)

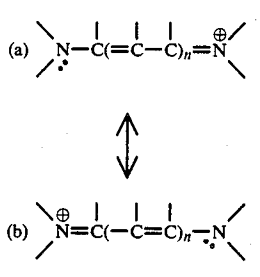

Amidinium-ion system (2)

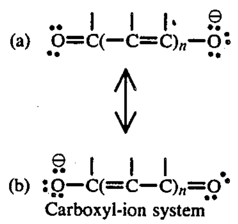

Carboxyl-ion system (3)

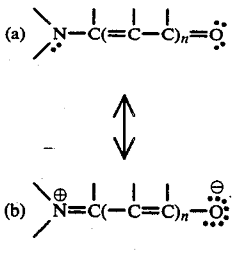

Amidic system

It will be appreciated that the two structures (a) and (b) for each system differ only in the way the electrons are disposed, not in the location of atoms. One or more carbon atoms in the chains may be replaced by nitrogen providing the conjugated structure is not disrupted. In actual dye examples the valencies shown unsatisfied in the skeletal formulae are completed as will be described and illustrated hereinafter.

In general, bleachable dyes for use in the invention will be of the general formula:

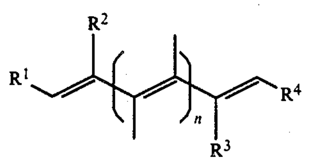

in which:

n is an integer of 1 to 5, and $R^1$ to $R^4$ are selected to provide an electron donor moiety at one end of the conjugated chain and an electron acceptor moiety at the other, and represent halogen, alkyl, aryl groups or heterocyclic rings any of which may be substituted, said groups generally containing up to 14 atoms selected from C, N, O and S; or $R^1$ and $R^2$ and/or $R^3$ and $R^4$ may represent the necessary atoms to complete optionally substituted aryl groups or heterocyclic rings, generally containing up to 14 atoms selected from C, N, O and S.

The conjugated chain is preferably composed of carbon atoms but may include one or more nitrogen atoms providing the conjugation is not disrupted. The free valencies on the chain may be satisfied by hydrogen or any substituent of the type used in the cyanine dye art including fused ring systems.

The particular selection of substituents $R^1$ to $R^4$ effects the light absorbance properties of the dye which may be varied to provide absorption peaks ranging from the ultraviolet (300 to 400 nm), near visible (400 to 500 nm), far visible (500 to 700 nm) and infrared (700 to 1100 nm). The absorption characteristics of the dyes do not significantly effect the sensitivity of the composition of the invention, which is governed by the particular selection of mesoionic compound.

Within the above general structure of dyes are various classes of dyes including:

(1) Cyanine dyes of the general formula:

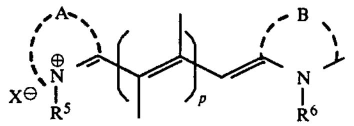

in which:

p is an integer of 0 to 5, $R^5$ and $R^6$ are independently hydrogen or substituents which may be present in conventional cyanine dyes, e.g. alkyl (preferably of 1 to 4 carbon atoms), etc., $X^-$ represents an anion, and A and B independently represent alkyl, aryl or heterocyclic groups or the necessary atoms to complete heterocyclic rings which may be the same or different. The groups A and B generally contain up to 14 atoms selected from C, N, O and S.

This class of dyes is very well known particularly in the silver halide photographic art and are the subject of numerous patents. General references to these dyes include *The Chemistry of Synthetic Dyes,* K. Venkataraman ed., Academic Press, Vol. 4 (1971) and *The Theory of the Photographic Process,* T. H. James, ed., MacMillan, Editions 3 and 4.

(2) Merocyanine dyes of the general formula:

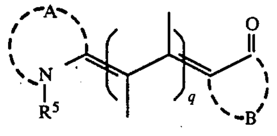

in which:

q is an integer of 0 to 5, $R^5$ and A are as defined above, and

B is as defined above or may complete a carbocyclic ring.

These dyes are also well known in the silver halide photographic art and are described in *The Theory of the Photographic Process,* referred to above.

(3) Oxonols of the general formula:

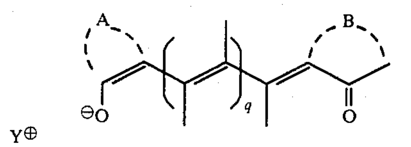

in which:

q is an integer of 0 to 5,

A and B may be the same or different and are as defined above in relation to cyanine and merocyanine dyes, and Y⊕ represents a cation.

Oxonol dyes are similarly well known in the silver halide photographic art and are disclosed in the above mentioned reference, *The Theory of the Photographic Process* and, for example, U.S. Pat. No. 2,611,696.

It is to be understood that these cyanine, merocyanine and oxonol dyes may bear substituents along the polymethine chain composed of C, N, O and S, and that these substituents may themselves join to form 5, 6 or 7 membered rings, or may bond with rings A and B to form further rings, possibly with aromatic character. Rings A and B may also be substituted by C, N, H, O and S containing groups.

Other known classes of dyes useful in the invention which possess an activated methylene chain include bisquinones, bisnaphthoquinones, hemicyanine, streptocyanine, anthraquinone, indamine, indoaniline and indophenol.

Preferred dyes for use in the invention are merocyanine and oxonol dyes. Examples of oxonol dyes include:

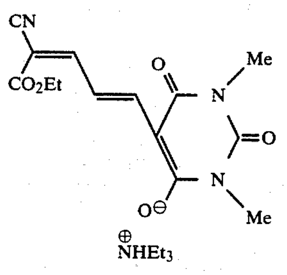

(yellow dye)

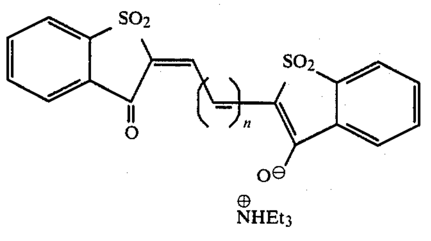

(n = 1, magenta dye
n = 2, cyan dye)

The cation of the oxonol dye need not be the iodonium ion and can be any cation including Li⊕, Na⊕ and K⊕ or quaternary ammonium cations, e.g. as represented by the formula:

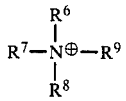

in which $R^6$ to $R^9$ may be selected from a wide range of groups including hydrogen, alkyl, preferably of 1 to 4 carbon atoms, aryl, e.g. phenyl, aralkyl of up to 12 carbon atoms. Preferably at least one of $R^6$ to $R^9$ is hydrogen and the rest are alkyl or aralkyl since such amines are readily available and allow easy synthesis of the dyes.

In some aspects of the invention, it is essential to immobilise the oxonol dye in the binder during the fixing process. This can be achieved by incorporation of a mordant in the form of the oxonol dye cation. Thus, any cationic polyelectrolyte may be used, e.g. those of the formula:

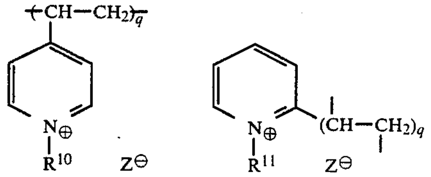

in which:

q is an integer, $R^{10}$ and $R^{11}$ independently represent hydrogen, alkyl, preferably containing 1 to 4 carbon atoms, groups, e.g. methyl, ethyl, or a group having a quaternary ammonium group at the end of an alkyl chain, e.g. $CH_2—CH_2—CH_2—N^{\oplus}(Me)_3Z^{\ominus}$; preferably hydrogen or alkyl ammonium, and $Z^{\ominus}$ represents an anion, e.g. acetate, chloride. With proper selection of the quaternary ammonium or pyridinium cations, such polymeric materials may also serve as the binder for the system.

It may be desirable to have a selection of $R^{10}$ and $R^{11}$ groups in the polymer. Preferably up to 80% of $R^{10}$ and $R^{11}$ groups are hydrogen to ensure compatibility with gelatin binders.

The dye-iodonium system has its greatest sensitivity at the $\lambda_{max}$ of the longest wavelength absorbance peak. Generally it is necessary to irradiate the system with radiation of wavelength in the vicinity of this $\lambda^{max}$ for bleaching to occur. Thus, a combination of coloured dyes may be used, e.g. yellow, magenta and cyan, in the same or different layers in an element and these can be selectively bleached by appropriate visible radiation to form a full colour image. Monochromatic or polychromatic images may be produced using the photosensitive materials of this invention with relatively short exposure times in daylight or sunlight or even artificial sources of light (e.g. fluorescent lamps or laser beams). The exposure time, for adequate results, for example when using a 0.5 kW tungsten lamp at a distance of 0.7 m, may be between 1 second to 10 minutes.

The iodonium salts used in the invention are compounds consisting of a cation wherein a positively charged iodine atom bears two covalently bonded carbon atoms, and any anion. Preferably the acid from which the anion is derived has a pKa <5. The preferred compounds are diaryl, aryl/heteroaryl or diheteroaryl iodonium salts in which the carbon-to-iodine bonds are from aryl or heteroaryl groups. Aliphatic iodonium salts are not normally thermally stable at temperatures above 0° C. However, stabilised alkyl phenyl iodonium salts such as those disclosed in *Chem. Lett.* 1982, 65–6 are stable at ambient temperatures and may be used in the invention.

Suitable iodonium salts may be represented by the formula:

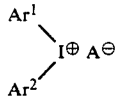

in which:

$Ar^1$ and $Ar^2$ independently represent carbocyclic or heterocyclic aromatic-type groups generally having from 4 to 20 carbon atoms, or together with the iodine atom complete a heterocyclic aromatic ring.

These groups include substituted and unsubstituted aromatic hydrocarbon rings, e.g. phenyl or naphthyl, which may be substituted with alkyl groups, e.g. methyl, alkoxy groups, e.g. methoxy, chlorine, bromine, iodine, fluorine, carboxy, cyano or nitro groups or any combination thereof. Examples of hetero-aromatic groups include thienyl, furanyl and pyrazolyl which may be substituted with similar substituents as described above. Condensed aromatic/hetero-aromatic groups, e.g. 3-indolinyl, may also be present.

$A^{\ominus}$ represents an anion which may be incorporated into $Ar^1$ or $Ar^2$.

Preferably $Ar^1$ and $Ar^2$ do not have more than two substituents at the α positions of the aryl groups. Most preferably $Ar^1$ and $Ar^2$ are both phenyl groups containing no α substituents.

The α positions of the aryl groups may be linked together to include the iodine atom within a ring structure, e.g.

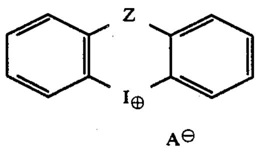

in which Z is an oxygen or sulphur atom. An example of such an iodonium salt is:

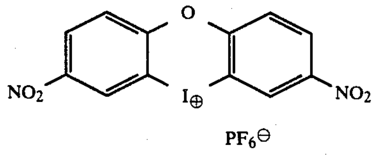

Other suitable iodonium salts include polymers containing the unit:

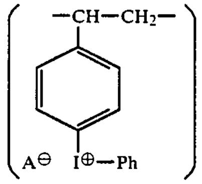

in which Ph represents phenyl. Examples of such polymers are disclosed in Yamada and Okowara, *Makromol. Chemie.* 1972, 152, 61–6.

Any anion may be used as the counter-ion $A^{\ominus}$ provided that the anion does not react with the iodonium salt. Suitable inorganic anions include halide anions, $HSO_4^{\ominus}$, and halogen-containing complex anions, e.g. tetrafluoroborate, hexafluorophosphate, hexafluoroarsenate and hexafluoroantimonate. Suitable organic anions include those of the formulae:

$RCOO^{\ominus}$ or $RSO_3^{\ominus}$ in which R is an alkyl or aryl group of up to 20 carbon atoms, e.g. a phenyl group, either of which may be substituted. Examples of such anions include $CH_3COO^{\ominus}$ and $CF_3COO^{\ominus}$.

$A^{\ominus}$ may be present in $Ar^1$ or $Ar^2$, e.g.

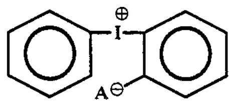

in which $A^{\ominus}$ represents $COO^{\ominus}$, etc.

Furthermore, $A^{\ominus}$ may be present in a molecule containing two or more anions, e.g. dicarboxylates containing more than 4 carbon atoms.

The most significant contribution of the anion is its effect upon the solubility of the iodonium salt in different solvents or binders. This criterion is also important for systems fixed by removal of the unreacted iodonium ion in an aqueous processing step where good solubility of the iodonium salt in water is essential.

Most of the iodonium salts are known, they may be readily prepared and some are commercially available. The synthesis of suitable iodonium salts is disclosed in F. M. Beringer et al, Journal of the American Chemical Society, 80, 4279 (1958). Previously, these salts have been used in cationically induced epoxy polymerization or radically induced monomer polymerization as disclosed, for example, in U.S. Pat. Nos. 3,741,769, 3,729,313, 3,808,006, 4,026,705, 4,228,232 and 4,250,053. Such polymerization systems may form the basis of imaging systems of the type utilizing a coloured toner which will selectively adhere only to the tacky unexposed areas which have not undergone polymerization.

The iodonium salts disclosed in the above referenced Patents have been sensitised with a wide range of dyes to increase speed and/or broaden spectral response and have been used as components in image forming systems in the absence of polymerizable monomers. However, heretofore there has been no disclosure nor indication in the prior art of a dye-bleach system suitable for image recording employing a bleachable dye and iodonium salt as the image recording medium.

The bleachable dye and iodonium salt are in reactive association on the support. Reactive association is defined as such physical proximity between the compounds as to enable a chemical reaction to take place between them upon exposure to light. In practice, the dye and iodonium salt are in the same layer or in adjacent layers on the support.

In general, the weight ratio of bleachable dye to iodonium salt in the element of the invention is in the range from 1:1 to 1:50, preferably in the range from 1:2 to 1:10.

The bleachable dye and iodonium salt may be applied to the support in a binder. Suitable binders are transparent or translucent, are generally colourless and include natural polymers. e.g. gelatin, gum arabic, synthetic resins, polymers and copolymers, e.g. polyvinyl acetals, cellulose esters, polyamides, polyacrylates, polymethacrylates, polyurethanes, polyepoxides, polycarbonates, polyvinylacetate, polyvinyl butyral, polyvinyl alcohol, polyvinyl pyrrolidone, polyvinylidene chloride, poly(4-vinyl-N-alkylpyridinium salt), and other film forming media. The binders may range from thermoplastic to highly crosslinked, and may be coated from aqueous or organic solvents or emulsion.

It is also possible for the binder to form part of the dye molecule as described above with reference to oxonol dyes. In practice, when separate binders are used the binder comprises from 50 to 98% by weight based on the total dry weight of binder, dye and iodonium salt.

Suitable supports for use in the invention are any stable substrate, including transparent film, e.g. polyester, paper e.g. baryta-coated photographic paper, and metallised film. Opaque vesicular polyester films are also useful.

It is not essential for the elements of the invention to comprise a separate support since a binder, e.g. a synthetic polymer, together with the dye and iodonium salts may be cast to form a self-supporting film.

The fixing of the radiation sensitive elements of the invention may be effected by destruction of the iodonium ion by disrupting at least one of the carbon-to-iodine bonds since the resulting monoaryl iodine compound is no longer sensitive to the dye. The conversion of the iodonium salt to its non-radiation sensitive form can be effected in a variety of fashions. Introduction of ammonia and amines in reactive association with the iodonium ion, or a reaction caused on heating, or UV irradiation of a nucleophilic anion such as $I^{\ominus}$, $Br^{\ominus}$, $Cl^{\ominus}$, $BAr_4^{\ominus}$ (tetra-arylboronide), $ArO^{\ominus}$ (e.g. phenoxide), or $4\text{-}NO_2C_6H_4CO_2^{\ominus}$, with the iodonium ion, will effect the conversion.

An alternative method of achieving post imaging stabilisation or fixing is to remove the iodonium ion from reactive association with the dye by washing with an appropriate solvent. For example, in the case of elements using mordanted oxonols and water soluble iodinium salts formulated in gelatin, after imaging, the iodonium salt is simply removed by an aqueous wash, which leaves the immobilised dye in the binder. The dye stability to light is then equivalent to that of the dye alone. An element in which the dye and iodonium salt is formulated in polyvinylpyridine may be treated with aliphatic ketones to remove the iodonium salt and leave the dye in the binder.

The elements of the invention have excellent ageing properties. Tests over a period of several months have shown that there is a minimal variation of maximum density, $D_{max}$, and photosensitivity when elements are stored in the dark in a refrigerator (3° to 5° C.) and under ambient conditions (18° to 20° C., relative humidity 50 to 70%).

A variety of conventional additives such as surfactants, antioxidants, stabilisers, plasticisers, ultraviolet absorbers, coating aids, may be used to prepare the elements of the invention to achieve benefit of their known properties.

The elements of the invention may be used for transparencies for overhead visuals, making enlarged copies of colour slides and related graphics applications, such as pre-press colour proof materials.

The thermally bleachable elements of the invention can be used to give transparency copies from a black on white original, e.g. printed or typed matter and more particularly a photocopy. For example, the elements, when placed film face down on a photocopy and passed through a 3M Thermofax machine set at the lightest control, are bleached in the areas corresponding to the black areas of the photocopy. Thus, a negative (clear on colour) of the black on white original is obtained which after fixing is ready for overhead projection. With suitable photographic negatives, this method could be used to assemble colour overlaps rapidly and conveniently. A water wash fixing step may be used to stabilise the element.

The invention will now be illustrated by the following Examples.

The oxidation potentials referred to in the Examples were measured with an Ag/AgCl/saturated KCl reference electrode.

EXAMPLES 1 TO 9

Effect of iodonium ion type on the reaction with a magenta dye

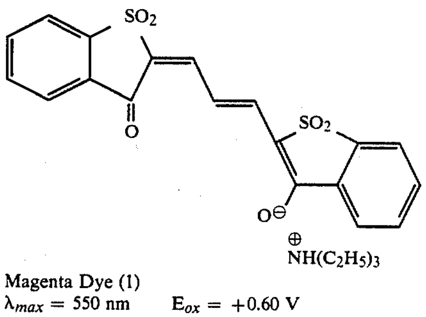

Magenta Dye (1)
$\lambda_{max}$ = 550 nm   $E_{ox}$ = +0.60 V

In all the Examples, 0.020 g of the magenta oxonol dye was coated as a solution in 10 ml of 10% by weight Butvar (B76) in butan-2-one (Butvar is a registered trade mark of Monsanto Company for polyvinylbutyral polymers). The dye solution was prepared in yellow light and the iodonium compounds tested were added in their respective proportions in red light. The photosensitive solution was then coated in red light at 100 μm wet thickness on a polyester base (75 μm). The sheets were air dried at 20° C. for 1 hour. A 2.5 cm square piece of each sample was then exposed over an area of 2.5 $mm^2$ with focussed light filtered, using a Kodak narrow band filter (551.4 nm: power output=$2.36\times10^{-3}$ $W/cm^2$) and the change in the transmission optical density with time was monitored using a Joyce Loebl Ltd. microdensitometer. A plot of transmission optical density versus time was made and the exposure time (t) for the optical density to fall from $D_{max}$ to ($D_{max}-1$) was determined. The energy required (E) was calculated as the exposure time (t)×power output (=$2.36\times10^{-3}$ W/cm$^2$): this gives an indication of the sensitivity of the elements.

The iodonium compounds used and the results obtained are reported in Table 1. In Examples 6 and 7, 1 ml of dimethylformamide was added to the coating solution to solubilise the iodonium salt.

TABLE 1

| Example No. | Iodonium salt | Weight of iodonium salt (g) | Optical Density $D_{max}$ | t (sec) | E (× $10^5$ mJ/m$^2$) |
|---|---|---|---|---|---|
| 1 | 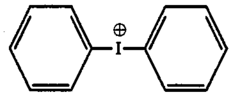 $PF_6^{\ominus}$ | 0.30 | 1.92 | 220 | 51.9 |
| 2 | 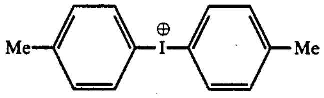 $PF_6^{\ominus}$ | 0.32 | 1.76 | 618 | 145 |
| 3 | 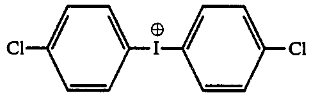 $PF_6^{\ominus}$ | 0.35 | 2.01 | 214 | 50.5 |
| 4 | 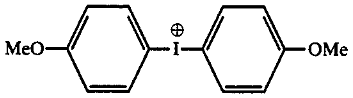 $PF_6^{\ominus}$ | 0.34 | 1.76 | 618 | 145 |
| 5 | 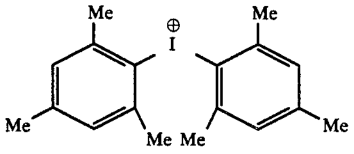 $PF_6^{\ominus}$ | 0.36 | 1.73 | 1257 | 300 |
| 6 | 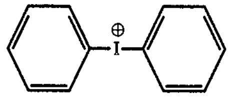 $PhSO_3^{\ominus}$ | 0.31 | 2.04 | 776 | 183 |
| 7 | 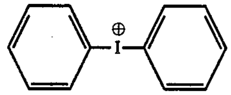 4-$MeC_6H_4SO_3^{\ominus}$ | 0.32 | 1.73 | 768 | 181 |
| 8 | 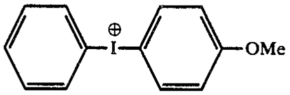 $CF_3CO_2^{\ominus}$ | 0.30 | 2.59 | 356 | 84.0 |

TABLE 1-continued

| Example No. | Iodonium salt | Weight of iodonium salt (g) | Optical Density $D_{max}$ | t (sec) | E ($\times 10^5$ mJ/m$^2$) |
|---|---|---|---|---|---|
| 9 | 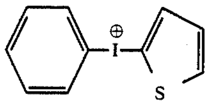 $CF_3CO_2^{\ominus}$ | 0.28 | 2.09 | 256 | 60.4 |

Comparison of the results, which are all acceptable for imaging systems, reveals:

(a) the anion of the iodonium salt helps to solubilise the onium ion (greater solubility leads to greater bleaching speeds), (b) substituents to the carbon-to-iodine bond on the iodonium ion inhibit the bleaching reaction, and (c) electron donating groups, e.g. S-alkyl, OMe, Me, on the aryl groups of the iodonium ion decrease the photosensitivity.

Under the same conditions and using triphenyl sulphonium hexafluorophosphate in place of the iodonium salt, bleaching was only observed at high temperature (>100° C.). Addition of 2,4,6-triphenylpyrylium trifluoromethane sulphonate or 1-(2,4-dinitrophenyl)-pyridinium chloride in place of the iodonium salt did not lead to bleaching of the oxonol.

Excellent ageing properties have been obtained with the elements. In Examples 1 and Examples 34 to 36, hereinafter, the variation in the standard deviation ,of the maximum density, $D_{max}$ and the photosensitivity remained well within 5% during storage assessments over a period of thirteen weeks. Thus, samples were retained in the dark in a refrigerator at 3° to 5° C., relative humidity (RH) 30%, in an enclosure 18° to 20° C., 50 to 70% RH, and under laboratory ambient conditions of 18° to 20° C., 50 to 70% RH: all exhibited minimal variation in the above properties indicating good dark shelf life.

EXAMPLES 10 TO 16

The effect of iodonium ion concentration

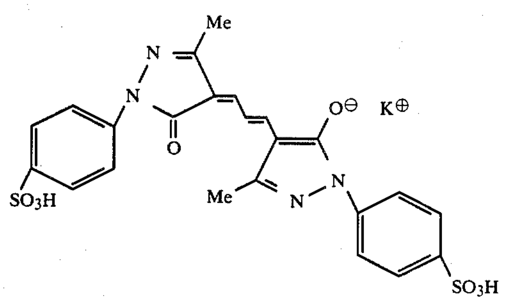

Magenta Dye (2)
$\lambda_{max}$ = 545 nm
(in Butvar (B76) layer)

4 ml of a 2% ethanolic solution of magenta dye (2) was added, in room light, to a 6 ml solution of Butvar B76 (1 g) in butan-2-one. In red light, varying proportions of the iodonium salts reported in Table 2 were added. The resulting lacquer was knife edge coated at 125 μm wet thickness on a 75 m polyester base and the photosensitive sheets dried in air at 20° C. for 1 hour. From the optical density versus time plots using filtered light 551.4 nm (with output $2.36\times10^{-3}$ W/cm$^2$), exposure time (t) were calculated and the energy value (E) determined as in Examples 1 to 9. The results are reported in Table 2.

TABLE 2

| Example No. | Iodonium salt | Weight of iodonium salt (dye:iodonium weight ratio) | $D_{max}$ | t (sec) | E ($\times 10^5$ mJ/m$^2$) |
|---|---|---|---|---|---|
| 10 | 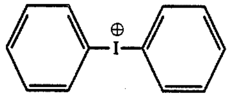 $PF_6^{\ominus}$ | 0.1 (ca 1:1) | 3.1 | 46 | 10.9 |
| 11 | 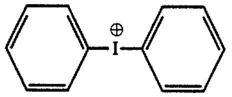 $PF_6^{\ominus}$ | 0.2 (1:2.5) | 2.9 | 19 | 4.5 |
| 12 | 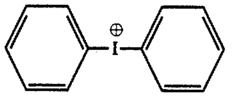 $PF_6^{\ominus}$ | 0.5 (1:6) | 3.1 | 11.5 | 2.7 |

TABLE 2-continued

| Example No. | Iodonium salt | Weight of iodonium salt (dye:iodonium weight ratio) | $D_{max}$ | t (sec) | E (× $10^5$ mJ/$m^2$) |
|---|---|---|---|---|---|
| 13 | 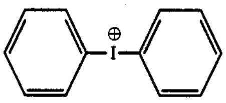 $PF_6^{\ominus}$ | 0.8 (1:10) | 2.3 | 8.5 | 2.0 |
| 14 | 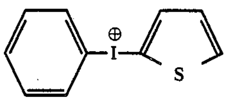 $CF_3CO_2^{\ominus}$ | 0.2 (1:2.5) | 3.0 | 56 | 13.2 |
| 15 | 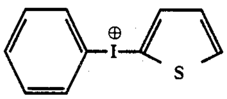 $CF_3CO_2^{\ominus}$ | 0.5 (1:6) | 2.5 | 32 | 7.6 |
| 16 | 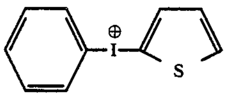 $CF_3CO_2^{\ominus}$ | 0.8 (1:10) | 2.8 | 22 | 5.2 |

The results indicate that increased addition of the iodonium salt leads to increased photosensitivity. An oxonol iodonium salt where the iodonium is the gegenion of the oxonol will show the best photosensitivity.

EXAMPLE 17

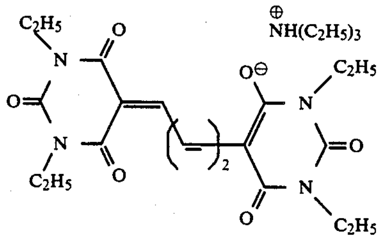

Blue Dye (3)
$\lambda_{max}$ = 605 nm (measured in gelatin layer)
$E_{ox}$ = +0.47 V 2 ml of 2% ethanolic blue dye (3) was added in room light to 8 ml aqueous solution at 55° C. of gelatin (1 g) and poly(4-vinyl-1-methyl-pyridinium methylsulphate) (0.2 g). The latter polymer was 10% molar methylated. 0.5 g (1:12 dye/onium w/w ratio) of phenyl(4-methoxyphenyl)iodonium trifluoroacetate was added in the dark and the mixture knife edge coated at 100 μm wet thickness onto polyester film (100 μm) which was subbed with a conventional wetting coat. After drying in the dark at 20° C. for 1 hour, a strip of the film was subjected to laser light of wavelength 632 nm. At the laser power density of $6.0 \times 10^2$ W/$cm^2$, a 10 μm diameter bleach spot required 1.5 seconds exposure. After exposure the film was fixed by washing (5 minutes) in water at 15° C.

EXAMPLES 18 TO 26

These Examples illustrate a range of dyes and the colour change upon exposure to light and reaction with diphenyl-iodonium hexafluorophosphate when mixed in acetone. A mixture of the dye (0.005 g) and iodonium salt (0.1 g) in 10 ml acetone was irradiated 1 foot from a 0.5 kW tungsten source. The results are reported in Table 3 whose $\lambda_{max}$ figures are measured in acetone solution.

TABLE 3

| Example No. | Dye Class | Dye | $E_{ox}$ V | $\lambda_{max}$ (nm) | Colour change |
|---|---|---|---|---|---|

TABLE 3-continued
| | | | | | |
|---|---|---|---|---|---|
| 18[1] | Oxonol | 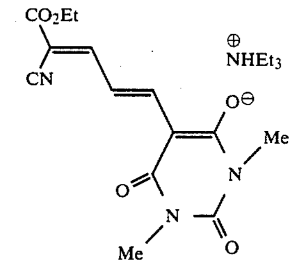 | +0.47 | 463 | Yellow to colourless |
| 19[2] | Oxonol | 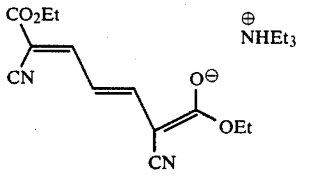 | +0.62 | 445 | Yellow to colourless |
| 20 | Mero-Cyanine | 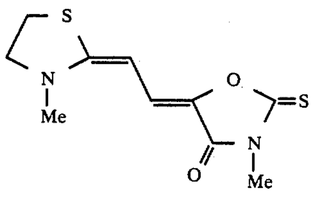 | +0.60 | 450 | Yellow to colourless |
| 21 | Oxonol | 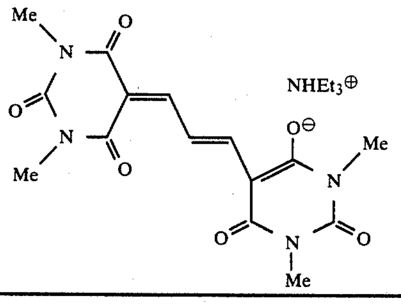 | +0.67 | 490 | Orange to colourless |
| Example No. | Dye Class | Dye | $\lambda_{max}$ (nm) | Colour change |
|---|---|---|---|---|
| 22 | Oxonol | 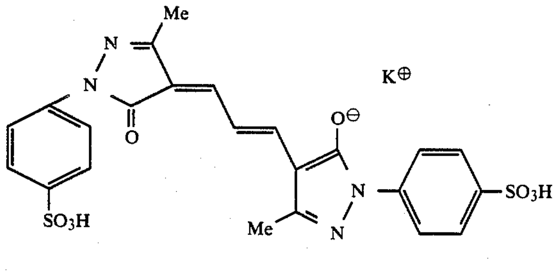 | 520<br>$E_{ox}$ = +0.37 V | Magenta to yellow |
| 23 | Oxonol | 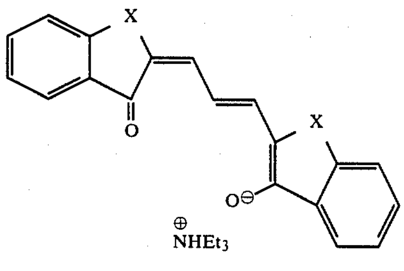 | A, X = $SO_2$ 545<br>$E_{ox}$ = +0.6 V<br>B, X = CO 555<br>$E_{ox}$ = +0.17 V | Magenta to pale yellow<br>Magenta to pale yellow |

TABLE 3-continued

| | | | | |
|---|---|---|---|---|
| 24 | | 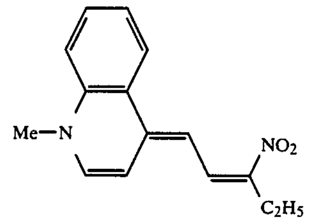 | 550 | Magenta to colourless |
| 25 | Oxonol | 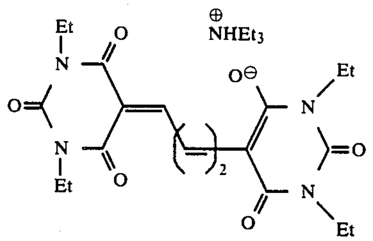 | 590<br>$E_{ox}$ = +0.47 V | Blue to colourless |
| 26 | Oxonol | 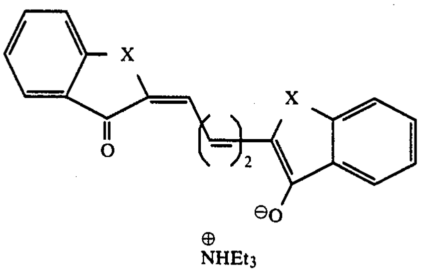 | A, X = $SO_2$ 645<br>$E_{ox}$ = +0.34 V<br>B, X = CO 655<br>$E_{ox}$ = +0.15 V | Cyan to pale yellow<br><br>Cyan to pale yellow |

Me = $CH_3$, Et = $C_2H_5$
(1)Preparation of dye as shown in Example 39.
(2)Preparation of dye as shown in Example 40.

EXAMPLES 27 TO 31

These Examples illustrate the use of various binders.

4 ml of 2% magenta dye (2) was added to a 6 ml solution of 10% w/v binder in an appropriate solvent. 0.2 g of diphenyliodonium hexafluorophosphate was added in red light and the mixture knife edge coated at 125 μm wet thickness. After drying in air at room temperature for 1 to 2 hours, optical density versus time plots on a Joyce Loebl microdensitometer using filtered light at 551.4 nm were determined. Exposure times (t) were calculated and thence the energy value (E) as in Examples 1 to 9. The results are reported in Table 4.

TABLE 4

| Example No. | Binder | Solvent | Polyester | $D_{max}$ | $D_{max-1}$ (sec) | E (× $10^5$ mJ/$m^2$) |
|---|---|---|---|---|---|---|
| 27 | Butvar (B-76) | MEK | Unsubbed | 3.0 | 19 | 4.5 |
| 28 | Saran* (poly vinylidene chloride) | MEK | Unsubbed | 2.9 | 23 | 5.4 |
| 29 | poly(methyl acrylate/ methyl methacrylate) | MEK | Unsubbed | 2.4 | 57 | 13.5 |
| 30 | polyvinyl-pyrrolidone | $H_2O$ | Subbed | 2.7 | 770 | 181 |
| 31 | gelatin | $H_2O$ | Subbed | 3.2 | 84 | 19.8 |

*Saran is a trade mark of the Dow Chemical Company.

EXAMPLE 32

Stabilisation by disruption of carbon-to-iodine bond

This Example illustrates the use of ammonia to stabilise the elements of the invention. The ammonia reacts with the light-sensitive iodonium salt and thus decreases the photosensitivity of the film.

4 ml of 2% magenta dye (2) was added to a 6 ml solution of 10% w/v poly(methylacrylate/methyl methacrylate) in butan-2-one. 0.5 g of diphenyliodonium hexafluorophosphate was added in red light and the resulting lacquer knife edge coated at 125 μm wet thickness. After drying in air, the film was exposed through a black and white transparency for 10 sec on an overheat projector (0.5 kW quartz iodine lamp) to give a magenta copy. The resulting film was exposed to ammonia vapour in the dark for 12 hours. Subsequent photosensitivity of the film was substantially reduced: determination of the energy values (E) in accordance with Examples 1 to 9 revealed a 17-fold increase ($4.7\times10^5$ mJ/$m^2$ to $80\times10^5$ mJ/$m^2$).

EXAMPLE 33

Stabilisation by removal of the iodonium salt

Blue dye (3) 0.04 g in ethanol (4 ml) was added to a photographic grade gelatin (1 g) solution in water (6 ml) at 55° C. containing aqueous Tergitol TMN10 (Union Carbide Company) non-ionic surfactant (10%, 0.3 ml), poly(4-vinyl-1-methylpyridinium methylsulphate) as in Example 17 (0.2 g) and 0.5 ml acetic acid. In green light phenyl(2-thienyl)-iodonium trifluoroacetate (1.0 g) was added. The blue solution was knife edge coated at 100 μm wet thickness on 100 μm subbed polyester. After chilling at 10° C. for 10 minutes, the coated sheet was dried in air at 20° C. for 2 hours. The film was exposed through a black and white transparency on an overhead projector (0.5 kW quartz iodine lamp) using an exposure of 60 seconds. A blue copy of the original resulted. The image film was fixed by washing in water at 18° C. for 3 to 5 minutes. After drying in air upon subsequent exposure to laboratory light no further bleaching was noticeable. The comparative grey scale and resolution of the copy were excellent.

EXAMPLES 34 TO 36

These three Examples demonstrate the utility of the imaging system described herein in colour proofing materials for the graphic arts industry.

The dyes in the quantities reported in Table 5 in 4 ml of ethanol were added to a solution of gelatin (1 g) and poly(4-vinyl-1-methylpyridiniummethyl-sulphate) as in Example 17 (0.2 g) in 6 ml of water at 55° C. 0.5 g of phenyl(4-methoxyphenyl)iodonium trifluoroacetate was added in red light to the solutions of yellow and magenta dyes and the same addition was made to the cyan solution in green light.

After the addition of aqueous Tergitol surfactant (10%, 0.3 ml), the solutions were coated at 75 μm thickness on subbed polyester, the coated sheets chilled to 10° C. for 10 minutes and then dried in air for 1 hours. Density versus time plots were measured as in Examples 1 to 9 using Kodak filters (output in brackets), respectively 461.6 nm ($5.41\times10^{-4}$ W/cm$^2$), 551.4 nm ($2.36\times10^{-3}$ W/cm$^2$) and 670.7 nm ($4.75\times10^{-3}$ W/cm$^2$) for Examples 35, 36 and 37 respectively. The results are reported in Table 5.

TABLE 5

| Example No. | Dye | Wt. (g) | $\lambda_{max}$ (nm) | $D_{max}$ | t (secs) | E ($\times 10^5$ mJ/m$^2$) |
|---|---|---|---|---|---|---|
| 34 | 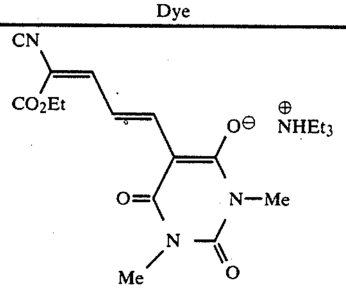 | 0.020 | 470 | 1.4 | 240 | 13.1 |
| 35 | 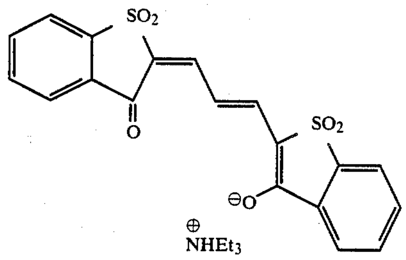 | 0.015 | 552 | 1.4 | 250 | 59.0 |
| 36 | 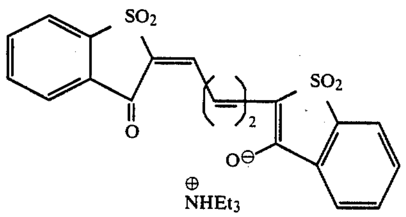 | 0.020 | 658 | 2.0 | 460 | 178.0 |

Imaging the samples with the appropriate colour separation positive transparency was achieved by contacting the transparency with coated sheet (coated side up) on a vacuum frame and exposing at 0.5 m to a unfocussed 1 kW tungsten halide source. After imaging, the film was washed with agitation in a water bath at 15° C. for 5 minutes. Drying in air and arranging the three samples, yellow/magenta/cyan, one on top of the other gave a colour proof with a very good grey scale (tonal reproduction) and resolution.

Identical samples were taped in the following order—magenta, yellow, cyan to a 35 mm colour transparency slide. The composite was then placed into the slide compartment of a slide projector with the coated sheets farthest from the quartz iodine projector source (240 W). After an exposure of 60 seconds, a positive full colour reproduction of the original slide resulted. The individual sheets were then washed in water at 15° C. for 5 minutes, dried in air and reassembled to give a stable copy of the slide.

EXAMPLE 37

A full-colour single sheet film element imageable by a tungsten visible source was constructed by coating one side of a 100 μm (subbed on both sides) polyester film with a 75 μm wet thickness cyan layer and on the other side of the film with a mixed magenta and yellow layer of the same wet thickness. The coating compositions comprised phenyl(2-thienyl)-iodonium trifluoroacetate and as the film-forming binder a mixture of gelatin and poly(4-vinyl-1-methylpyridinium methylsulphate) as in Example 17 (1:0.2 by weight).

The dyes used and the weight of the components are reported in Table 6.

TABLE 6

| Layer | Dye(s) | Wt. of dye (g) | Wt. of binders Gelatin/PVP (g) | Wt. of Iodonium (g) |
|---|---|---|---|---|
| 1 Cyan | 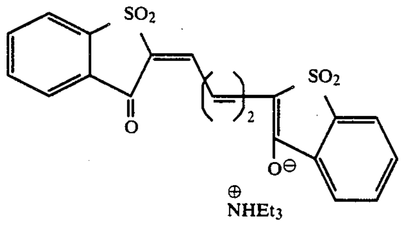 | 0.020 | 1/0.2 | 0.5 |
| Magenta | 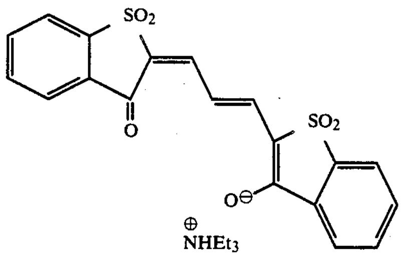 | 0.010 | | |
| 2 | | | 1/0.2 | 1.0 |
| Yellow | 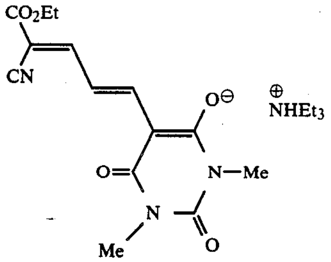 | 0.020 | | |

After drying in the dark for 4 hours at room temperature, the multicolor film element was placed in contact with a full colour transparency with the magenta/yellow coating next to the transparency and the composite exposed through the transparency in a slide projector having a 240 watt source bulb for 45 to 50 seconds. A full colour reproduction of the original was obtained. The copy was rendered stable to light by a wash in water for 3 to 5 minutes.

The yellow dye reported in Table 6 is a novel compound.

EXAMPLE 38

A solution of the yellow dye in Example 18 (0.02 g) in ethanol (4 ml) was added to a solution of 1 g gelatin and 0.3 g poly(4-vinyl-1-methylpyridinium methylsulphate) as in Example 17 in 10 ml water and 0.5 ml acetic acid at 40° C. 0.3 ml Tergitol-4 (10% aqueous solution) was added to this yellow lacquer. 0.9 g of 4-methoxyphenyl-phenyl-iodonium trifluoroacetate in 1 ml dimethyl-formamide was added in red light. The solution was then knife-edged coated at 100 μm wet thickness onto a 125 μm subbed polyester base and dried in air for 0.5 hours at ca 15° to 20° C. to give a yellow film, $\lambda_{max}$ 474 nm, $D_{max}=2.1$.

An inch square piece was exposed with an Ar-ion laser operating at 488 nm onto a spot area of 8 $\mu m^2$. Dwell times varied between 5 ms to 18 μs; the minimum dwell time required to bleach a spot of diameter 2.5 μm was 18 μs. Thus, the energy/unit area requirements for this film were $9\times10^6$ $mJ/m^2$ to bleach from $D_{max}$ of 2 to 0.10.

EXAMPLE 39

Preparation of:

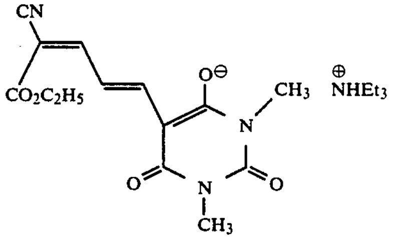

To 5-acetanilino-allylidene-1,3-dimethylbarbituric acid (6.4 g, 20 mmol) and excess ethyl cyanoacetate (5.0 g) in 50 ml ethanol was added triethylamine (5 ml). The mixture was heated for 0.5 hour, by which time a red solution resulted. The UV-visible spectrum of this solution in ethanol showed two bands: major $\lambda_{max}$ 465 nm and minor $\lambda_{max}$ 490 nm. On cooling, orange crystals of the minor product (1.0 g) were isolated: the minor product was the symmetrical bis-barbiturate trimethin oxonol. The mother liquors were diluted with diethyl ether (200 ml) and cooled to give yellow "fluffy" crystals of 5-(ethyl-cyanoacetyl-allylidene)-1,3-dimethylbarbiturate triethylammonium salt, $\lambda_{max}$ (EtOH) 460 nm, $\epsilon 6.5\times 10^4$. The yield was 3.2 g, 40%.$E_{ox}$ is +0.47 V (ref. Ag/AgCl in sat. KCl).

Empirical formula: $C_{20}H_{30}N_4O_5$

| | C % | H % | N % |
|---|---|---|---|
| Calculated | 59.00 | 7.44 | 13.78 |
| Found | 59.03 | 7.40 | 13.98 |

EXAMPLE 40

Preparation of

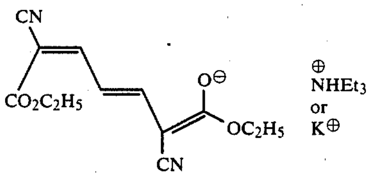

Diethyl 2,6-dicyano-2,4,6-heptatriene-1,7-dicarboxylate triethylammonium or potassium salt.

A mixture of 3-anilinoacrolein anil (2.22 g, 10 mmol), ethyl cyanoacetate (4.8 g, 42 mmol) and triethylamine (3.3 ml) in 30 ml ethanol was heated for 6 hours. The reaction was followed by UV-visible spectrometer monitoring for completion of the reaction which is observed by the formulation of a single band at 450 nm (EtOH). Evaporation of the solvent gave a red oil which was washed several times with ether to give a red viscous oil (blue reflecting), yield ca 5 g, $\lambda_{max}$ (EtOH) 445 nm, $\epsilon 8\times 10^4$.

A sample of the red oil (1 g) was dissolved in ethanol with potassium acetate (1 g). The mixture was evaporated and the potassium salt taken up in acetone and reprecipitated with ether to give ca 0.5 g of the potassium salt, $\lambda_{max}$ (EtOH) 445 nm, $\epsilon=1.01\times 10^5$, $E_{ox}$ is +0.62 V (vs Ag/AgCl sat. KCl reference). Empirical formula: $C_{13}H_{13}N_2O_4K$

| | C % | H % | N % |
|---|---|---|---|
| Calculated | 52.0 | 4.36 | 9.32 |
| Found | 49.5 | 4.61 | 9.95 |

Low carbon due to residual potassium acetate.

EXAMPLE 41

Bleaching of an I.R. Absorbing Dye

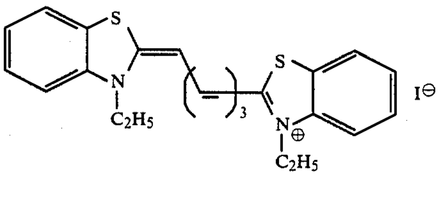

N.I.R. Cyanine Dye
$\lambda_{max}$ (acetone) 762 nm 1 mg of the above dye was dissolved in 5 ml of acetone and additional with diphenyliodonium hexafluorophosphate (50 mg). The mixture was irradiated for 5 seconds at a distance of 1 foot from a 0.5 kW tungsten lamp. The following Table 7 shows the absorbances of the dye (a) alone, (b) with the iodonium salt in the dark, and (c) after irradiation with tungsten light.

TABLE 7

| Composition | Absorbance at 700 nm | Absorbance at 750 nm |
|---|---|---|
| Dye in acetone | 0.84 | 2.36 |
| Dye + iodonium salt in acetone in dark | 0.95 | 2.50 |
| Dye + iodonium salt in acetone after irradiation | 0.22 | 0.32 |

Thus, suitable I.R. dyes in combination with iodonium salts may be used to form I.R. sensitive elements useful, for example, as I.R. masks, I.R. bleachable antihalation layers, and optical data storage.

EXAMPLE 42

(a) Preparation of:

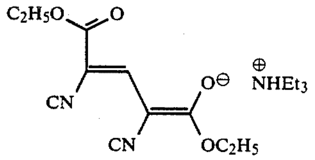

Dye UV-1

A mixture of dimethylformaldehyde dimethoxyacetal (2.0 g), ethyl cyanoacetate (5.0 g) and triethylamine (10 ml) in ethanol (30 ml) was heated at reflux for 12 hours. The solution was cooled, and diluted with diethyl ether (100 ml) and petroleum ether (40°/60° C. 50 ml). The resulting "opaque" solution was cooled for 24 hours, yielding dense, white needles of the dye as the $NHEt_3$ salt: 1.8 g; $\lambda_{max}$ (ethanol) 355 nm ($\epsilon$=4./5$\times 10^5$); $E_{ox}$ +0.45.

Empirical formula: $C_{17}H_{27}N_3O_4$

| | C % | H % | N % |
|---|---|---|---|
| Calculated | 60.5 | 8.07 | 12.45 |
| Found | 59.9 | 7.80 | 12.37 |

(b) Dye bleach system

A mixture of UV-1 (1 mg) and diphenyliodonium hexafluorophosphate (0.01 g) in acetone (5 ml ) was irradiated 1 foot from a 4 kW metal halide source for 40 seconds. The UV spectrum was monitored before and after irradiation to show the "bleaching" of the UV dye. The results are reported in the following Table 8.

TABLE 8

| Composition | Absorbance at 356 nm |
|---|---|
| UV-1 + iodonium salt in acetone | 3.72 |
| UV-1 + iodonium salt in acetone | |
| - 10 units exposure | 3.12 |
| - 40 units exposure | 0.28 |

Thus, elements comprising suitable UV absorbing dyes and iodonium salts may be used to form UV masks, UV-bleachable antihalation layers, etc.

EXAMPLE 43

A mixture of Dye UV-1 (0.3 g), diphenyliodonium hexafluorophosphate (0.3 g) and Butvar B76 (1 g) dissolved in butan-2-one (15 ml) was coated in red light onto a 25μ polyester film. The absorbence of this layer at 360 nm was approximately 3.8 which decreased to 3.3 after heating to 150° C. for 30 seconds.

Such an element or mixture may be used for heat-bleachable antihalation layers, UV masks, etc., or for a method of fixing a visible image by heat destruction of the excess iodonium ion.

EXAMPLE 44

Five Dyes in a Single Layer

In some applications, e.g. copies of 35 mm colour slides, it is necessary to attain $D_{max}$ values of 2.0 to 2.5. Oxonol dyes have a peak half-width of 45 nm: thus to achieve neutral densities of 2.0, high dye densities are required.

The required density is achieved by the addition of two extra dyes termed "blocking dyes" at 500 and 600 nm. This Example illustrates a typical five-dye, single layer element, in which the five dyes are matched in sensitivity to the requirements of the exposure source.

To a solution at 50° C. of gelatin (5.4 g) and poly(4-vinyl-1-methylpyridinium methylsulphate) (0.4 g) in acetic acid (0.5 ml) and aqueous Tergitol No. 10 (2.0 ml, 10%) were added in ethanol (10 ml) and water (2 ml) the following dyes:

(A) Dye of Example 19 0.03 g
(B) Dye of Example 21 0.02 g
(C) Dye of Example 23B 0.025 g,
(D) Dye of Example 25 0.01 g, and
(E) Dye of Example 26B 0.04 g.

To this resulting dark blue solution, in the dark, was added 4-methoxyphenyl-phenyliodonium trifluoroacetate (2.5 g) in N,N-dimethyl-formamide (3.0 ml) and chrome alum (0.05 g in 1 ml $H_2O$). The mixture was placed in the loop-coater vessel and loop-coated on subbed polyester to give 2 m×0.15 m of coated film. The film was dried in an air cupboard at 21° C. for 2 hours.

Table 9 records the $\lambda_{max}$ of each of the five dyes in the composite coating, measured by a transmission spectrometer. The transmission optical density of each dye at or close to its $\lambda_{max}$ is recorded in Table 9 as $D_{max}$. The energy, E, required to reduce the optical density of each dye at its $\lambda_{max}$ by 1 optical density unit on irradiation with light of a wavelength corresponding to the $\lambda_{max}$ is also recorded.

The five dye composite was found to have an optical density of at least 2, balanced to a good neutral, averaged across the spectrum from 430 to 700 nm.

The film was placed in contact with a 35 mm colour slide in the focussed beam of a tin halide or Xenon source for 30 seconds. The resulting copy was fixed by a water wash (5 minutes/20° C.) and drying in air. Good separation of yellow, magenta, red and blue were obtained: cyan and green colours were weak.

TABLE 9

| Dye | A | B | C | D | E |
|---|---|---|---|---|---|
| $\lambda_{max}$ | 454 | 514 | 563 | 604 | 672 |
| $D_{max}$ | 3.4 | 2.1 | 3.4 | 2.3 | 4.3 |
| Energy (E) ($\times 10^5$ mJ/m$^2$ | 15 | 21 | 36 | 9 | 3 |

We claim:

1. A compound of either of the formulae:

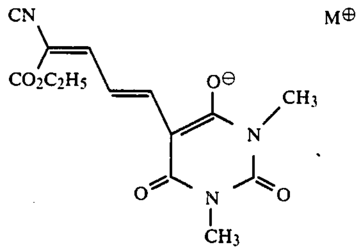

and

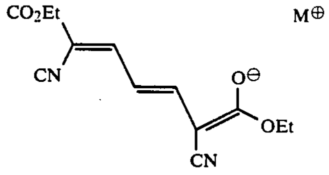

in which M⊕ represents a cation.

2. A compound having the formula:

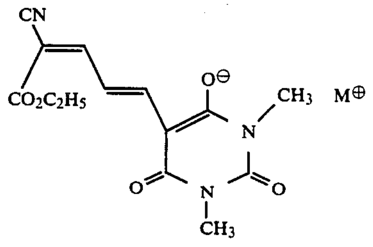

in which M⊕ represents a cation.

3. A compound having the formula:

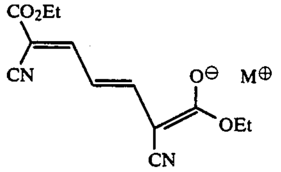

in which M⊕ represents a cation.

4. The compound of claim 2 in which M⊕ is an iodonium ion.

5. The compound of claim 3 in which M⊕ is selected from the group consisting of Li⊕, Na⊕, K⊕, and quaternary ammonium.

6. The compound of claim 3 in which M⊕ is an iodonium ion.

7. A compound having the formula:

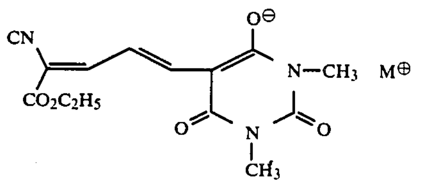

in which M+ represents a cation selected from the group consisting of Li+, Na+, K+, and quaternary ammoniums.

* * * * *